United States Patent [19]

Fráter et al.

[11] 4,435,207
[45] Mar. 6, 1984

[54] QUINYLOXY-PHENYLOXY-OXIME ESTER COMPOUNDS HAVING HERBICIDAL ACTIVITY

[75] Inventors: Georg Fráter, Greifensee; Milos Suchy, Pfaffhausen; Jean Wenger, Uster; Paul Winternitz, Greifensee, all of Switzerland

[73] Assignee: Hoffmann-La Roche Inc., Nutley, N.J.

[21] Appl. No.: 323,784

[22] Filed: Nov. 23, 1981

[30] Foreign Application Priority Data

Nov. 26, 1980 [CH] Switzerland .................. 8750/80
Oct. 1, 1981 [CH] Switzerland .................. 6328/81

[51] Int. Cl.³ .................. A01N 43/40; C07D 215/22
[52] U.S. Cl. .................. 71/94; 71/92; 546/157; 546/292; 546/295; 546/300; 544/343
[58] Field of Search .................. 71/94, 108; 546/157

[56] References Cited

U.S. PATENT DOCUMENTS

| | | | |
|---|---|---|---|
| 3,718,653 | 2/1973 | Hamer | 260/283 S |
| 3,923,810 | 12/1975 | Harrington et al. | 260/256.5 R |
| 4,227,009 | 10/1980 | Koch et al. | 71/108 |
| 4,309,210 | 1/1982 | Quadranti et al. | 71/93 |
| 4,329,488 | 5/1982 | Frater et al. | 71/108 |
| 4,334,914 | 6/1982 | Hiraga et al. | 71/108 |

FOREIGN PATENT DOCUMENTS

| | | | |
|---|---|---|---|
| 3295 | 8/1979 | European Pat. Off. | 71/108 |
| 2830141 | 1/1980 | Fed. Rep. of Germany | 71/94 |
| 5143970 | 10/1980 | Japan | 546/157 |
| 372190 | 11/1963 | Switzerland | 71/108 |

*Primary Examiner*—Donald G. Daus
*Assistant Examiner*—G. Hendricks
*Attorney, Agent, or Firm*—Jon S. Saxe; George M. Gould; John J. Maitner

[57] ABSTRACT

Oxime ester compounds of the formula

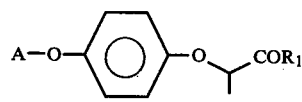

I wherein A is one of the groups

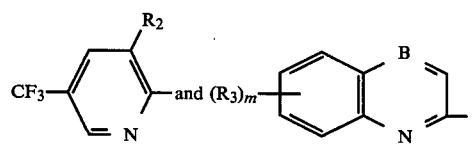

Ia        Ib wherein B is —CH= or nitrogen and $R_1$ is one of the groups

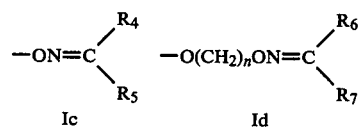

Ic        Id wherein $R_2$–$R_7$, m and n are as hereinafter set forth, processes for their preparation, herbicidal compositions containing these compounds as the active ingredient and methods of use of the herbicidal compositions are disclosed.

20 Claims, No Drawings

QUINYLOXY-PHENYLOXY-OXIME ESTER COMPOUNDS HAVING HERBICIDAL ACTIVITY

SUMMARY OF THE INVENTION

The invention relates to oxime esters of the formula

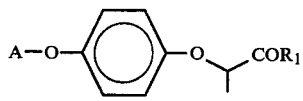

I wherein A is one of the groups

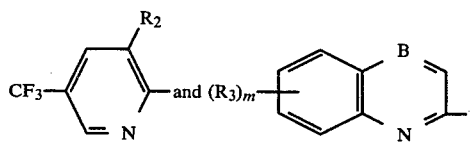

in which $R_2$ signifies hydrogen, halogen or trifluoromethyl and $R_3$ is hydrogen, halogen or trifluoromethyl, m is 1 or 2, B is —CH= or nitrogen, and wherein $R_1$ is one of the groups

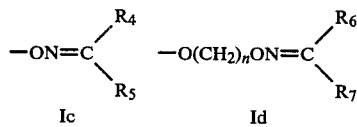

wherein when A is a group of formula Ia or a group of formula Ib in which B is —CH=, $R_4$, $R_5$, $R_6$ and $R_7$ are lower alkyl, cycloalkyl with 3 to 6 carbon atoms, lower alkylcarbonyloxy-lower-alkyl, lower alkoxy or lower alkylthio or $R_4$ and $R_5$ or $R_6$ and $R_7$ together with the carbon atom to which they are attached are a cycloalkyl group with 4 to 7 carbon atoms and when B is nitrogen, $R_6$ and $R_7$ are as described above, $R_4$ and $R_5$ are lower alkylcarbonyloxy-lower-alkyl, lower alkoxy or lower alkylthio or $R_4$ is lower alkyl or cycloalkyl with 3 to 6 carbon atoms and $R_5$ represents lower alkylcarbonyloxy-lower-alkyl, lower alkoxy or lower alkylthio, wherein n is 1 or 2, and wherein $R_4$ and $R_6$ can also be hydrogen.

In another aspect, the invention relates to herbicidal compositions and methods.

DETAILED DESCRIPTION OF THE INVENTION

The invention is directed to oxime esters of the formula

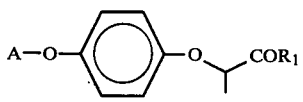

I wherein A is one of the groups

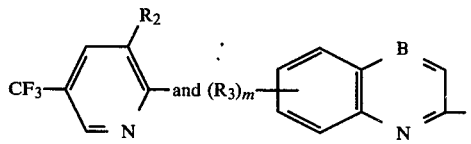

in which $R_2$ is hydrogen, halogen or trifluoromethyl and $R_3$ is hydrogen, halogen or trifluoromethyl, m is 1 or 2, B is —CH= or nitrogen, and wherein $R_1$ is one of the groups

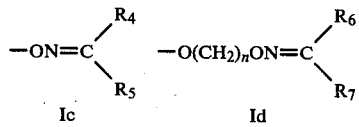

wherein when A is a group of formula Ia or a group of formula Ib in which B is —CH=, $R_4$, $R_5$, $R_6$ and $R_7$ are lower alkyl, cycloalkyl with 3 to 6 carbon atoms, lower alkylcarbonyloxy-lower-alkyl, lower alkoxy or lower alkylthio or $R_4$ and $R_5$ or $R_6$ and $R_7$ together with the carbon atom to which they are attached are a cycloalkyl group with 4 to 7 carbon atoms and when B is nitrogen, $R_6$ and $R_7$ sare as described above, $R_4$ and $R_5$ are lower alkylcarbonyloxy-lower-alkyl, lower alkoxy or lower alkylthio or $R_4$ is lower alkyl or cycloalkyl with 3 to 6 carbon atoms and $R_5$ is lower alkylcarbonyloxy-lower-alkyl, lower alkoxy or lower alkylthio, and wherein n is 1 or 2 and wherein $R_4$ and $R_6$ can also be hydrogen.

The invention is also directed to processes for the preparation of the compounds of formula I as well as herbicidal compositions which contain, as the active ingredient, a compound of formula I, and methods for their use. The compounds have both pre-emergence and post-emergence herbicidal activity.

As used herein, the term "lower alkyl" encompasses both straight-chain and branched-chain hydrocarbon groups containing 1-6 carbon atoms such as methyl, ethyl, propyl, isopropyl, butyl, isobutyl, tert.-butyl and the like. Alkyl groups with 1-3 carbon atoms are preferred.

The term "halogen" encompasses fluorine, chlorine, bromine and iodine, and preferably chlorine and iodine.

Of the cycloalkyl groups with 3-6 or 4-7 carbon atoms, namely cyclopropyl, cyclobutyl, cyclypentyl, cyclohexyl and cycloheptyl, cyclohexyl is preferred.

In the lower alkoxy or lower alkylthio groups, the alkyl portion can contain 1-6, preferably 1-3, carbon atoms.

Preferred compounds of formula I are those wherein A is the group Ib and B is —CH=. Further, there are preferred those compounds in which $R_4$, $R_5$, $R_6$ and $R_7$ represent alkyl groups with 1 or 2 carbon atoms, especially methyl.

Among the compounds of formula I, wherein A is the group Ib, wherein B is —CH=, and $R_1$ is the group Ic, those compounds are preferred, wherein $R_3$ is different from hydrogen, i.e. wherein $R_3$ is halogen or trifluoromethyl.

Preferred compounds of formula I are:

Acetone O-[2-[p-[[(6-chloro-2-quinolyl)oxy]phenoxy]-propionyl]oxime, ethyl O-[2-[p-[(6-bromo-quinolyl)oxy]phenoxy]-propionyl]acetohydroxamate,

[(isopropylideneamino)oxy]methyl 2-[p-[(6-fluoro-2-quinolyl)oxy]phenoxy]propionate and

[(isopropylideneamino)oxy]methyl 2-[p-[(6-chloro-2-quinoxalinyl)oxy]phenoxy]propionate, especially the D-isomers of these compounds.

The compounds of formula I are prepared by one of the procedures described below.

A. Reacting an acid of the formula

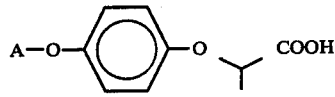

II wherein A is as described above or a reactive derivative of this acid, with an oxime of the formula $R_4R_5CNOH$   III

wherein $R_4$ and $R_5$ are as described above.

The term "reactive derivative of the acid" encompasses an acid halide, especially the acid chloride, or an acid anhydride.

The esterification of an acid of formula II with an oxime of formula III is preferably carried out in a suitable inert solvent, especially at room temperature or at an elevated temperature. A preferred temperature range is from about $-10°$ to about $+100°$ C., especially between 20° to 70° C.

When an acid halide is used as the reactive derivative of the acid, the reaction with the oxime is carried out at room temperature and in the presence of an acid acceptor, for example, a tertiary amine such as pyridine, triethylamine or the like, or in alkaline solution according to Schotten-Baumann. The corresponding ester is obtained in high yield. The acid chlorides are the preferred acid halides. The reaction is preferably carried out in the presence of an inert solvent such as benzene, toluene, petroleum ether or the like, or according to Schotten-Baumann in alkaline solution.

When the anhydride of the acid of formula II is used, the corresponding alkanecarboxylic acid ester of formula I can be prepared in high yield by heating the anhydride with the oxime of formula III in the presence of a base, preferably an alkali metal carbonate. Sodium carbonate is especially preferred.

When a free acid of formula II is used as the starting material, the reaction with an oxime of formula III, is conveniently carried out in the presence of dicyclohexylcarbodiimide. In carrying out this reaction, the acid of formula II is dissolved in an inert organic solvent such as a chlorinated hydrocarbon, for example, dichloromethane, chloroform, carbon tetrachloride, trichloroethane or the like, an ether, for example, diethyl ether, diisopropyl ether, dioxan, or the like, an aromatic hydrocarbon, for example, benzene, toluene, xylene, or the like, and thereafter the oxime of formula III is suspended in this solution. The dicyclohexylcarbodiimide is dissolved in the same solvent and the solution is added to the reaction mixture. The reaction is carried out at a temperature between 0° and the boiling point of the reaction mixture, preferably between room temperature and 50°. The reaction is completed after about 2 hours and the reaction mixture is filtered. The filtrate is evaporated, and the residue is purified by, e.g. recrystallization or chromatography.

B. Reacting a compound of the general formula

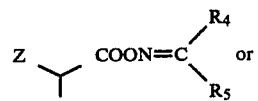

IV

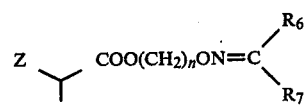

V wherein Z is a leaving group and $R_4$, $R_5$, $R_6$ and $R_7$ are as described above, with a compound of the formula

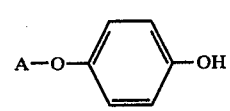

VI wherein A is as described above, or an alkali metal salt thereof.

In formulas IV and V above, Z represents a leaving group, especially chlorine, bromine, iodine, mesyloxy and tosyloxy. The leaving group may also be a reactive hydroxy group, especially a hydroxy group activated by reaction with triphenylphosphine and azodicarboxylic acid or an ester thereof especially diethyl azodicarboxylate [see for example Bull. Chem. Soc. Japan 46, 2833 (1973) or Angew. Chem. 88, 111(1976)].

In accordance with this procedure, a compound of formula IV or V is reacted with a compound of formula VI or an alkali metal salt thereof in a manner known per se, and if required in the presence of a base. The reaction is conveniently carried out in an inert organic solvent such as a hydrocarbon, for example, benzene, toluene, or the like, an ether, for example diethyl ether, tetrahydrofuran, dimethoxyethane, or hexamethylphosphoric acid triamide or the like. The temperature and pressure are not critical and the reaction is preferably carried out at a temperature between $-20°$ and the reflux temperature of the reaction mixture, preferably between $-10°$ and 30° C.

Since the oxime ester compounds of formula I have asymmetric carbon atoms in the α-position to the carbonyl group, these compounds can exist in optically active isomeric forms. In fact, these esters can have more than one asymmetric carbon atom. The racemic compounds can be resolved in their dextrorotatory and laevorotatory isomers using known procedures as, for example, that described in Industrial and Engineering Chemistry 60(8), 12–28 (1968). The racemic mixtures as well as the isomers all have herbicidal activity with the D-isomer having the highest activity followed by the racemic mixture and the L-isomer. For example, it has been found the the D-isomer of acetone O-[2-[p-[5-(trifluoromethyl)-2-pyridyl]oxy]phenoxy]propionyl]oxime has a higher activity than the racemic mixture.

The isomers especially the D-isomers can also be prepared by synthesis from corresponding optically active starting materials.

In addition, and as a result of the nitrogen-carbon double bond in the oxime group

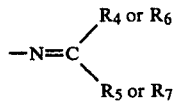

it is also possible to have in each case two geometric isomers when $R_4$ and $R_5$ or $R_6$ or $R_7$ are different. These isomers, the syn- and anti-form, can also be isolated in certain cases.

This invention is also directed to herbicidal compositions which comprise inert carrier material and, as the active ingredient, one or more compounds of formula I. These herbicidal compositions suitably contain, as the inert carrier material, at least one of the following ingredients: carrier materials, wetting agents, inert diluents and solvents.

The compounds of formula I are, in general, water-insoluble. Thus, the usual methods of formulation of insoluble materials can be followed. For example, the compounds can be dissolved in a water-immiscible solvent such as a high-boiling hydrocarbon which conveniently contains dissolved emulsifiers so that the solution acts as a self-emulsifiable oil when added to water.

The compounds of formula I can also be mixed with a wetting agent, with or without an inert diluent, to form a wettable powder which is soluble or dispersible in water. The compounds can alternatively be mixed with an inert diluent to form a solid or pulverulent product.

Suitable inert diluents are solid inert media including pulverulent or finely divided solids such as clays, sand, talc, mica, fertilizers and the like. The resulting compositions can be either dusts or materials of relatively large particle size.

Wetting agents, suitable for use with the compounds of this invention, can be anionic, cationic or nonionic.

Examples of anionic wetting agents include soaps, fatty sulfate esters such as dodecyl sodium sulfate, octadecyl sodium sulfate and cetyl sodium sulfate, fatty aromatic sulfonates such as alkylbenzene-sulfonates and butylnaphthalene-sulfonates, and the more complex fatty sulfonates such as the amide condensation products of oleic acid and N-methyltaurine or the sodium sulfonate of dioctyl succinate.

Examples of cationic wetting agents include cetyltrimethylammonium bromide and the like.

Examples of nonionic wetting agents include, for example, condensation products of fatty acids, fatty alcohols or fatty substituted phenols with ethylene oxides; fatty acid esters and ethers of sugars or polyhydric alcohols; condensation products of sugars or polyhydric alcohols with ethylene oxide; and block copolymers of ethylene oxide and propylene oxide.

The herbicidal compositions of this invention can also be used in aerosol form using, in addition to the propellant gas, carrier material comprising a co-solvent and a wetting agent. Suitable propellant gases include the polyhalogenated alkanes such as dichlorodifluoromethane.

The herbicidal compositions of this invention can also contain other active ingredients such as synergistic agents, insecticides, bactericides, other herbicides, fungicides, plant growth regulators and fertilizers. Such combination preparations are suitable for increasing the activity or for broadening the spectrum of activity.

The compounds of this invention are useful as both pre-emergent and post-emergent herbicides. They are particularly suitable in combatting weed grasses such as slender foxtail (*Alopecurus myosuroides*) and types of millet such as cock's foot (*Echinochloa crus-galli*), great foxtail millet (*Setaria faberii*) and hair-like millet (*Panicum capillare*) in cereals. They are suitable for use against these weed grasses especially in cereals such as barley, oats and wheat, and in rice, cotton, soya, sugar beet and vegetable crops. The compounds of this invention are especially active against Alopecurus.

The pre-emergent and post-emergent herbicidal compositions of this invention are especially preferred for combatting weeds in sugar beet crops. For example, acetone O-[2-[p-[5-trifluoromethyl-2-pyridyl]oxy]-phenoxy]propionyl]oxime applied at a concentration of 1.25 kg/ha is sufficiently active against weed grasses without damaging the sugar beet crop.

In general, the compounds of this invention are effective as herbicides when applied at a concentration of about 0.1 to about 6 kg/ha with the preferred concentration range being from about 0.6 to about 2.0 kg/ha. An especially preferred application rate is from about 1 to about 1.5 kg/ha.

The utility in corn crops of compounds of formula I wherein $R_3$ is trifluoromethyl is limited in cereal growing since these compounds are somewhat phytotoxic. However, these compounds are particularly suitable for combatting weed grasses in rice, cotton, soya, sugar beet and vegetable crops.

The herbicidal compositions of this invention can be in the form of concentrates suitable for storage or shipment. Such compositions can contain, e.g. from about 2% to about 90% by weight, based on the weight of the total composition, of one or more of the active compounds of this invention. These concentrates can be diluted, with the same or different inert carrier material, to concentrations which are suitable for actual use. Ready-to-use compositions can contain concentrations of from 2% to 80% by weight of the active ingredient. Particularly preferred concentrations of active ingredients in the herbicidal compositions of this invention are from about 2% to about 80% by weight and preferably from about 50% to about 80% by weight.

The following Examples illustrate the present invention.

EXAMPLE 1

3.4 g of 2-[p-[[(5-trifluoromethyl)-2-pyridyl]-oxy]-phenoxy]propionic acid are suspended in 50 ml of dichloromethane and 1.1 g of acetone oxime are added at room temperature. Thereafter, 2.1 g of dicyclohexylcarbodiimide, dissolved in 20 ml of dichloromethane, are added dropwise over a period of 10 minutes; the temperature rises to about 40° C. The mixture is stirred at room temperature for an additional 2 hours. The mixture is filtered and the filtrate is evaporated to dryness on a rotary evaporator to yield acetone O-[2-[p-[[5-(trifluoromethyl)-2-pyridyl]oxy]phenoxy]propionyl]oxime; $n_D^{24} 1.5202$.

In an analogous manner compounds of formula I are prepared from appropriate starting materials according to the procedure described above.

(1) D-2-[p-[(3-chloro-5-trifluoromethyl-2-pyridyl)-oxy]phenoxy]propionic acid and acetone oxime yield acetone O-[D-2-[p-[(3-chloro-5-trifluoromethyl-2-pyridyl) oxy]phenoxy]propionyl]oxime; (2) D-2-[p-[[5-(trifluoromethyl)-2-pyridyl]-oxy]phenoxy]propionic acid and isopropylideneamino-oxy-ethanol yield 2-[(isopropylideneamino)oxy]-ethyl D-2-[p-[[5-(trifluoromethyl)-2-pyridyl]oxy]phenoxy]-propionate;

(3) D-2-[[5-(trifluoromethyl)-2-pyridyl]oxy]-phenoxy]propionic acid and 2-butanone oxime yield 2-butanone O-[D-2-[[5-(trifluoromethyl)-2-pyridyl]oxy]-phenoxy]propionyl]oxime (4) D-2-[[5-(trifluoromethyl)-2-pyridyl]oxy]-phenoxy]propionic acid and cyclohexanone oxime there is obtained cyclohexanone O-[D-2-[p-[[5-(trifluoromethyl)-2-pyridyl]oxy]phenoxy]propionyl]oxime.

The 2-[p-[[5-(trifluoromethyl)-2-pyridyl]oxy]-phenoxy]propionic acid used as the starting material in the first paragraph of this Example can be obtained as follows.

0.7 g of a 50% suspension of sodium hydride in mineral oil is washed twice in an inert gas atmosphere with 5.0 ml of tetrahydrofuran each time. The washed suspension is added to 15.0 ml of tetrahydrofuran and treated dropwise with a solution of 3.5 g of p-[(5-trifluoromethyl-2-pyridyl)oxy]-phenol dissolved in 30.0 ml of dimethylformamide. 3.5 g of ethyl L-2-[(p-tolylsulphonyl)oxy]propionate in 20.0 ml of dimethylformamide are subsequently added dropwise to the mixture. The mixture is stirred at room temperature for an additional 12 hours, thereafter poured onto ice and exhaustively extracted with ether. The extract is washed with water, dried over sodium sulphate and evaporated under reduced pressure. The residual ethyl D-2-[p-[[5-(trifluoromethyl)-2-pyridyl]oxy]phenoxy]-propionate can be purified by adsorption on silica gel; $[\alpha]_D^{20} + 21.7°$ (CHCl$_3$, c=1.1%).

5.3 g of ethyl D-2-[p-[[5-(trifluoromethyl)-3-pyridyl]oxy]phenoxy]propionate are suspended in 20 ml of methanol, treated with 1.7 g of potassium hydroxide dissolved in 50 ml of water, and stirred at room temperature for 1.5 hours. For the working-up, the mixture is diluted with 200 ml of water, acidified with hydrochloric acid and extracted with ether. The ether extract is washed with water, dried over sodium sulphate and evaporated under reduced pressure. The residual D-2-[p-[[5-(trifluoromethyl)-2-pyridyl]oxy]oxy]phenoxy]-propionic acid can be purified by adsorption on silica gel; $[\alpha]_D^{22} = +18.3°$ (CHCl$_3$, c=1.1%).

In an analogous manner, from p-[(3-chloro-5-trifluoromethyl-2-pyridyl)oxy]-phenol and ethyl L-2-[(p-tolylsulphonyl)oxy]propionate there is obtained ethyl D-2-[p-(3-chloro-5-trifluoromethyl-2-pyridyl)oxy]-phenoxy]propionate and therefrom there is obtained D-2-[p-[(3-chloro-5-trifluoromethyl-2-pyridyl)-oxy]-phenoxy]propionic acid as well as the corresponding D-isomer of the oxime ester.

EXAMPLE 2

5.4 g of D-2-[p-[(6-chloro-2-quinolyl)oxy]phenoxy]-propionic acid and 2 g of acetone oxime are dissolved in 30 ml of methylene chloride and treated at room temperature with 3.2 g of dicyclohexylcarbodiimide. In so doing, the temperature rises briefly to 34° C. After 20 minutes, the mixture is filtered and the filtrate is evaporated. The residual oil is chromatographed on silica gel to yield 5.9 g of acetone O-[D-2-[p-[(6-chloro-2-quinolyl)oxy]phenoxy]propionyl]oxime; $[\alpha]_D^{22} = +67.9°$ (CHCl$_3$, c=1.3%).

The D-2-[p-[(6-chloro-2-quinolyl)oxy]phenoxy]-propionic acid used as the starting material can be obtained as follows.

108 g of 4-(6-chloro-2-quinoyloxy)-phenol are dissolved with 110 g of triphenylphosphine and 50 g of ethyl L-lactate in 200 ml of N,N-dimethylformamide and treated slowly while cooling with 100 g of diisopropyl diazocarboxylate. The mixture is then extracted with water and ether, the organic phase is dried and evaporated. The residual oil is chromatographed on silica gel with haxane/ether (1:2) to yield 100 g of methyl D-2[p-(6-chloro-2-quinolyloxy)phenoxy]propionate; $[\alpha]_D^{22} = +28.8°$ (CHCl$_3$, c=1.8%).

80 g of the ester obtained according to the preceding paragraph are heated at 70° C. for 30 minutes in methanolic calcium hydroxide solution (40 g of calcium hydroxide in 400 ml of methanol). Thereupon, half of the methanol is removed by evaporation and the residue is extracted with water and ether. The aqueous phase is acidified with phosphoric acid and the product crystallizes out. The crystals are filtered off and recrystallized from toluene/pentane to yield 60 g of D-2-[p-[(6-chloro-2-quinolyl)oxy]phenoxy]propionic acid with a melting point of 130° C.; $[\alpha]_D^{22} = +15.6°$ (CHCl$_3$, c=1.72%).

EXAMPLE 3

In a manner analogous to Example 1 of 2, by reacting D-2-[[5-(trifluoromethyl)-2-pyridyl]oxy]phenoxy]-propionic acid with acetic acid ethyl ester oxime there is obtained ethyl 3-[[[D-2-[[5-(trifluoromethyl)-2-pyridyloxy]phenoxy]propionyl]oxy]imino]butyrate.

EXAMPLE 4

1.76 g of [(isopropylideneamino)-oxy]methyl L(−)-lactate, 2.65 g of triphenylphosphine and 2.72 g of p-[(6-chloro-2-quinoxalinyl)oxy]phenol are dissolved at 0° C. in 10 ml of absolute tetrahydrofuran. To the resulting solution, 1.75 g of diethylazodicarboxylate is added dropwise with cooling and stirring. Thereafter the mixture is stirred for ½ hour, poured into 100 ml of water and extracted twice with ethyl acetate. The organic phase is washed with dilute hydrochloric acid and water, dried over sodium sulfate and evaporated. The residue is chromatographed on 20 times its volume of silicagel using hexane/ethyl acetate 8:2 as the eluant. The eluted product is recrystallized from methylene chloride/n-hexane to yield [(isopropylideneamino)oxy]-methyl D-1-[p-[(6-chloro-2-quinoxalinyl)-oxy]-phenoxy]propionate. $[\alpha]_D^{20} + 20,05$ (c=1.93% in CHCl$_3$) m.p. 75°–77° C.

In an analogous manner there is obtained from a 1:1 mixture of p-[(6-fluoro-2-quinoxalinyl)oxy]phenol and p-[(7-fluoro-2-quinoxalinyl)-oxy]phenol, a 1:1 mixture of [(isopropylideneamino)oxy]methyl D-1-[p-[(6-fluoro-2-quinoxalinyl)oxy]phenoxy]propionate and [(isopropylidene-amino)oxy]methyl D-2-[p-[(7-fluoro-2-quinoxalinyl)oxy]phenoxy]propionate $[\alpha]_D^{22}$ +21.18 (c=1.14% in CHCl$_3$).

EXAMPLE 5

An emulsifiable concentrate is prepared by mixing the following ingredients with one another:

| | |
|---|---|
| Compound of formula I | 500 g |
| Condensation product of an alkyl-phenol and ethylene oxide; calcium dodecylbenzenesulphonic acid | 100 g |
| Epoxidated soya oil with an oxirane oxygen content of about 6% | 25 g |
| Butylated hydroxytoluene | 10 g |

The mixture is made up to 1 liter with xylene.
I claim:

1. An oxime ester of the formula

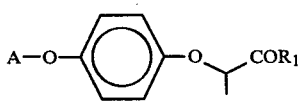

wherein A is

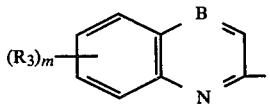

in which $R_3$ is hydrogen, halogen or trifluoromethyl, m is 1 or 2, B is —CH=, and wherein $R_1$ is a group of the formula

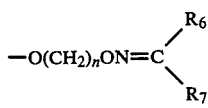

wherein $R_6$ and $R_7$ are lower alkyl, cycloalkyl with 3 to 6 carbon atoms, lower alkylcarbonyloxy-lower alkyl, lower alkoxy or lower alkylthio or $R_6$ and $R_7$ together with the carbon atom to which they are attached are a cycloalkyl group with 3 to 7 carbon atoms, and wherein n is 1 or 2, and wherein $R_6$ can also be hydrogen.

2. A compound according to claim 1, wherein $R_6$ and $R_7$ are lower alkyl, cycloalkyl with 3 to 6 carbon atoms, lower alkylcarbonyloxy-lower alkyl, lower alkoxy or lower alkylthio or $R_6$ and $R_7$ together with the carbon atom to which they are attached are a cycloalkyl group with 4 to 7 carbon atoms and wherein n is 1 or 2.

3. A compound according to claim 1 or claim 2, wherein A is group Ib in which B is —CH=.

4. A compound according to claim 3, wherein $R_1$ is group Id.

5. A compound according to claim 4, wherein $R_6$ and $R_7$ are alkyl groups with 1 or 2 carbon atoms.

6. A compound according to claim 5 wherein $R_6$, and $R_7$ are methyl.

7. A D-isomer of a compound according to claim 1.

8. Acetone O-[2-[p-[(6-chloro-2-quinolyl)oxy]-phenoxy]-propionyl oxime.

9. Ethyl O-[2-[p-[(6-bromo-quinolyl)oxy]phenoxy]-propionly]acetohydroxamate.

10. [(Isopropylideneamino)oxy]methyl 2-[p-[6-fluoro-2-quinolyl)oxy]phenoxy]propionate.

11. The D-isomers of the compounds according to any one of claim 8, 9 or 10.

12. A herbicidal composition which comprises an inert carrier material, and as the active ingredient, an amount of one or more of the compounds of claim 1 which is effective as a herbicide.

13. A herbicidal composition of claim 12, wherein the active ingredient is Acetone O-[2-[p-[(6-chloro-2-quinolyl)oxy]phenoxy]-propionyl oxime.

14. A herbicidal composition of claim 12 where the active ingredient is Ethyl O-[2-[p-[(6-bromo-quinolyl)oxy]phenoxy]-propionyl]acetohydroxamate.

15. A herbicidal composition of claim 12 where the active ingredient is [(Isopropylideneamino)oxy]methyl 2-[p-[(6-fluoro-2-quinolyl)oxy]phenoxy]propionate.

16. A method for combatting weeds which comprises applying, to the locus to be protected, a herbicidally effective amount of the composition of claim 12.

17. A method for combatting weeds which comprises applying, to the locus to be protected, a herbicidally effective amount of the composition of claim 13.

18. A method for combatting weeds which comprises applying, to the locus to be protected, a herbicidally effective amount of the composition of claim 14.

19. A method for combatting weeds which comprises applying, to the locus to be protected, a herbicidally effective amount of the composition of claim 15.

20. An oxime ester of the formula

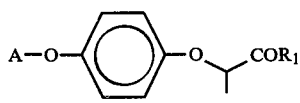

wherein A is

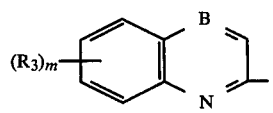

in which $R_3$ is hydrogen, halogen or trifluoromethyl, m is 1 or 2, B is —CH=, and wherein $R_1$ is a group of the formula

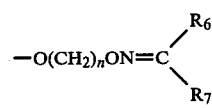

wherein $R_6$ and $R_7$ are lower alkyl, cycloalkyl with 3 to 6 carbon atoms, lower alkylcarbonyloxy-lower alkyl, lower alkoxy or lower alkylthio or $R_6$ and $R_7$ together with the carbon atom to which they are attached are a cycloalkyl group with 3 to 7 carbon atoms, and wherein n is 1 or 2, and wherein $R_6$ can also be hydrogen.

* * * * *